United States Patent
Li et al.

(10) Patent No.: US 12,320,794 B1
(45) Date of Patent: Jun. 3, 2025

(54) LAYOUT OPTIMIZATION METHOD OF WATER QUALITY MONITORING POINTS BASED ON RF-C-SOM CLUSTERING ALGORITHM

(71) Applicant: Hunan University Of Technology and Business, Changsha (CN)

(72) Inventors: Huan Li, Changsha (CN); Xintong Ouyang, Loudi (CN); Yongmei Xu, Bengbu (CN); Liang Chen, Changsha (CN); Xinxing Li, Ganzhou (CN); Changqing Su, Changsha (CN); Shengbo Gu, Beijing (CN); Yang Chen, Xiangxiang (CN); Jiayin Guo, Hangzhou (CN); Linfeng Jin, Changsha (CN)

(73) Assignee: Hunan University Of Technology and Business, Changsha (CN)

( * ) Notice: Subject to any disclaimer, the term of this patent is extended or adjusted under 35 U.S.C. 154(b) by 0 days.

(21) Appl. No.: 18/963,782

(22) Filed: Nov. 29, 2024

(30) Foreign Application Priority Data

Mar. 1, 2024 (CN) .......................... 202410233377.5

(51) Int. Cl.
*G01N 33/18* (2006.01)
*G06N 20/20* (2019.01)

(52) U.S. Cl.
CPC ............. *G01N 33/18* (2013.01); *G06N 20/20* (2019.01)

(58) Field of Classification Search
None
See application file for complete search history.

(56) References Cited

U.S. PATENT DOCUMENTS

| | | | |
|---|---|---|---|
| 2020/0231466 A1* | 7/2020 | Lu | G01N 33/18 |
| 2021/0097217 A1* | 4/2021 | Liu | G06N 20/20 |
| 2024/0201159 A1* | 6/2024 | Amit | G01N 33/18 |

OTHER PUBLICATIONS

Wang Yixu, et al., "Self-organizing map random forest coupling model based spatial heterogeneity evaluation of water quality in the watershed", Acta Scientiae Circumstantiae, Jun. 2020, pp. 2278-2285, vol. 40, No. 6.

* cited by examiner

*Primary Examiner* — Lisa M Caputo
*Assistant Examiner* — Cynthia L Davis

(57) ABSTRACT

A layout optimization method of water quality monitoring points based on a RF-C-SOM clustering algorithm includes: preprocessing collected water quality data to obtain preprocessed water quality data that are used as data, and using water quality categories as labels to train a random forest model to determine feature importance of water quality indicators; selecting important features based on the feature importance and model training accuracy, performing dimensionality reduction on the preprocessed water quality data to obtain dimension-reduced data; performing a fuzzy clustering on the dimension-reduced data to obtain a water quality section classification result, and based on it, determining initial weight values of a self-organizing mapping algorithm; initializing neurons and training a self-organizing mapping network model with the initial weight values; obtaining a point clustering result through the self-organizing mapping network model; and conducting a water quality index evaluation for the point clustering result before and after screening.

5 Claims, 2 Drawing Sheets

LAYOUT OPTIMIZATION METHOD OF WATER QUALITY MONITORING POINTS BASED ON RF-C-SOM CLUSTERING ALGORITHM

CROSS-REFERENCE TO RELATED APPLICATION

This application claims priority to Chinese Patent Application No. 2024102333775, filed Mar. 1, 2024, which is herein incorporated by reference in its entirety.

TECHNICAL FIELD

The disclosure relates to the technical field of layout optimizations of water quality monitoring points, and more particularly to a layout optimization method of water quality monitoring points based on a random forest—clustering—self-organizing mapping (RF-C-SOM) clustering algorithm.

BACKGROUND

Water is a basic element for the survival of all living things on Earth, and water resources play a crucial role in the sustainable development of regions and even countries. A research of water resources carrying capacity plays a practical role in realizing the harmony between human and the water resources and breaking through the bottleneck of the water resources restricting social development. In recent years, with the development of society and the change of environment, people's awareness of environmental protection has been continuously increasing, and government's effort in controlling water pollution has been continuously strengthened. Water quality monitoring plays a crucial role for us to grasp the quality of water timely and accurately. A selection of water quality monitoring points is the most critical first step. A reasonably designed layout of the water quality monitoring points can not only completely represent a current water quality situation, but also avoid too many unnecessary monitoring points, saving labor and resources.

With the advent of the big data era, machine learning has been rapidly developed and widely applied in various fields, including the environment field. In the past, the selection of water quality monitoring points often continued to apply old points from many years ago, and relevant specifications and requirements are general and poorly operational, which may lead to incorrect selection or redundancy in the selection of water quality monitoring points.

SUMMARY

In order to solve the aforementioned technical problems, the disclosure provides a layout optimization method of water quality monitoring points based on a RF-C-SOM clustering algorithm. This method combines a random forest algorithm from a supervised learning algorithm and a fuzzy clustering method to optimize a self-organizing mapping network. It analyzes the water quality at various cross-sections, selects and optimizes the monitoring points, enhances the accuracy of the monitoring points, improves efficiency, and saves labor and resources.

In order to achieve the aforementioned purpose, the disclosure provides the layout optimization method of the water quality monitoring points based on the RF-C-SOM clustering algorithm, which includes:

step 1, preprocessing collected initial water quality data to obtain preprocessed water quality data;

step 2, training a random forest model by taking the preprocessed water quality data as data and water quality categories as labels to determine feature importance of water quality indicators;

step 3, based on the feature importance and an accuracy of the random forest model training, selecting important features and performing dimensionality reduction on the preprocessed water quality data to obtain dimension-reduced data;

step 4, performing a fuzzy clustering on the dimension-reduced data to obtain a classification result of a water quality cross-section; step 5, based on the classification result of the water quality cross-section, determining initial weight values of a self-organizing mapping algorithm;

step 6, based on the initial weight values, initializing neurons and training a self-organizing mapping network model;

step 7, obtaining a point clustering result through the self-organizing mapping network model; and step 8, evaluating a water quality index by combining the initial water quality data with the point clustering result.

In an embodiment, the method is executable by one or more processors. In addition, the layout optimization method further includes:

obtaining target water quality monitoring points after completing the evaluation in the step 8, and setting sensors at each target water quality monitoring point for water quality monitoring in real time or periodically, and the sensors may include: a pH sensor, a dissolved oxygen sensor, a conductivity sensor, a turbidity sensor, a permanganate index sensor, an electrochemical sensor, and a nutrient sensor.

In addition, the layout optimization method further includes: establishing additional water quality monitoring points in a target water area which is determined based on the water quality index, the target water area may include river downstream, near residential areas, and nature reserves, and setting warning devices at the additional monitoring points, which automatically send alert messages through text message to residents in a vicinity of the target water area (such as polluted water area) when detecting abnormal water quality (such as the water quality is polluted), and simultaneously send a location of the target water area to relevant monitoring personnel, to achieve early warning; and the warning device may include a processor and a global positioning system (GPS) chip connected to the processor.

In an embodiment, the initial water quality data include potential of hydrogen (PH), dissolved oxygen, conductivity, turbidity, a permanganate index, ammonia nitrogen, total phosphorus and total nitrogen.

In an embodiment, a method of preprocessing the collected initial water quality data to obtain the preprocessed water quality data includes: for continuous missing values of each indicator of the collected initial water quality data, directly deleting the continuous missing values, and for an individual missing value of each indicator of the collected initial water quality data, adopting an attribution method and using an average of the indicator to fill in the individual missing value of the indicator to repair the individual missing value of the indicator, thereby obtaining processed initial water quality data; and in order to eliminate an impact of different dimensions and orders of magnitude, performing a Z-score standardization on the processed initial water quality data to obtain the preprocessed water quality data according to the formula as follows:

$$b_{ij} = \frac{a_{ij} - \bar{a}_j}{\delta_j}$$

where $a_{ij}$ represents a value of a $j^{th}$ indicator on an $i^{th}$ day, $\bar{a}_j$ represents a sample mean of the $j^{th}$ indicator, and $\delta_j$ represents a standard deviation of the $j^{th}$ indicator.

In an embodiment, a method of performing the dimensionality reduction on the preprocessed water quality data to obtain the dimension-reduced data includes: dividing the preprocessed water quality data into a training set and a test set in a ratio of 7:3, and using the water quality categories as the labels to train the random forest model;
  sampling from all training samples to obtain a sample set by using a bootstrap sampling method with replacement, and using the sample set to generate a decision tree; calculating impurities based on a Gini coefficient, determining an optimal node and an optimal branching method of the decision tree by selecting an optimal feature of an impurity indicator, and calculating the accuracy of the random forest model; and
  calculating importance of feature variables by utilizing an out-of-bag (oob) error generated by oob data to obtain top-ranked feature variables in terms of the importance.

In an embodiment, a method of calculating the impurities based on the Gini coefficient is:

$$Gini(t) = 1 - \sum_{i=0}^{c-1} p(i|t)^2$$

where c represents a number of the water quality categories, t represents a given feature node, and p(i|t) represents a proportion of a label category i at the feature node t.

In an embodiment, a method of calculating the importance of feature variables by utilizing the oob error generated by the oob data is:

$$\text{importance} = \sum_{i=1}^{N} \frac{(erroob2 - erroob1)}{N}$$

where N represents a number of the decision tree in a random forest.

In an embodiment, a method of performing the fuzzy clustering on the dimension-reduced data to obtain the classification result of the water quality cross-section includes:
  S1, initializing a clustering algorithm, and determining initial parameters and variables;
  S2, initializing a membership degree matrix U by using a random number between [0,1], and making the membership degree matrix U satisfy a constraint condition $\Sigma_{i=1}^{c} U_{ij} = 1$, where $U_{ij}$ represents a membership degree of a sample point $x_i$ and a cluster center $C_j$;
  S3, obtaining a fuzzy classification of a water quality dataset (i.e., the dimension-reduced data) through an iterative optimization of an objective function, using a method of Lagrange multipliers to obtain a minimum value of the objective function under a constraint condition, and calculating an updated membership degree matrix U and an updated cluster center C according to calculation formulas as follows:

$$j(U,V) = \Sigma_{i=1}^{n} \Sigma_{j=1}^{n} u_{ij}^{m} d(x_i, c_j)^2 \quad (1)$$

$$u_{ij} = \frac{1}{\sum_{k=1}^{c} \left(\frac{d(x_i, c_j)}{d(x_i, c_k)}\right)^{\frac{2}{m-1}}} \quad (2)$$

$$C_j = \frac{\sum_{i=1}^{n} u_{ij}^{m} x_i}{\sum_{i=1}^{n} u_{ij}^{m}} \quad (3)$$

where the formula (1) represents the objective function J of a Fuzzy C-Means (FCM) algorithm, and $d(x_i, c_j)$ represents an Euclidean distance between the water quality sample point $x_i$ and the cluster center $C_j$; the formula (2) represents the updated membership degree matrix U; and the formula (3) represents the updated cluster center $C_j$;
  a formula of the Euclidean distance is:

$$d(X, C) = \sqrt{\sum_{i=1}^{n}(x_i - y_i)^2}$$

where d(X,C) represents the Euclidean distance between a water quality sample point X and a cluster center C, $x_i$ (i=1, 2, ..., n) is a $i^{th}$ coordinate of the water quality sample point X, and $y_i$ (i=1, 2, ..., n) is a $i^{th}$ coordinate of the cluster center C; and
  S4, repeating S3 until the objective function J meets an iteration termination condition $\|J^l - J^{l-1}\| \le \varepsilon$, at this time, an iterative center of data no longer changing significantly, and outputting results of the cluster center and the data membership degree matrix.

In an embodiment, a method of obtaining the point clustering result through the self-organizing mapping network model includes:
  initializing a two-dimensional grid structure, where each node represents a cluster center;
  initializing samples in a dataset (i.e., the dimension-reduced data) based on a fuzzy clustering result (i.e., the classification result of the water quality cross-section obtained in step 4), where samples belonging to a same category are assigned a same initial weight vector, and then updating weights through a network topology structure;
  in each iteration, selecting an input sample, finding a node closest to a node corresponding to the input sample, and adjusting update magnitudes of a best matching unit and its neighboring nodes; and
  through continuous iteration, adjacent nodes forming clusters in a feature space, and ultimately creating a topological mapping of the data.

In an embodiment, a method of updating the weights includes:

$$W_j^{k+1} = W_j^k + \eta^k g_{ij} * (x_i - W_j^k)$$

where $W_j^k$ represents a weight of a $j^{th}$ neuron node at a $k^{th}$ iteration, $\eta^k$ represents a learning rate at the $k^{th}$ iteration, and $g_{ij}$ represents an update magnitude of the $j^{th}$ neural node of a winning neighborhood corresponding to an $i^{th}$ sample.

In an embodiment, a method of calculating the update magnitudes of the nodes with a winning neighborhood (also referred to as winner's neighborhood) according to a neighborhood function is:

$$g(i,j) = e^{-\frac{(c_x-i)^2}{2\sigma_{(k)}^2}} e^{-\frac{(c_y-j)^2}{2\sigma_{(k)}^2}}$$

where ($c_x$, $c_y$) represents the best matching unit, and $\sigma_{(k)}$ represents a winning radius at the $k^{th}$ iteration.

The technical effect of the disclosure is: The disclosure provides the layout optimization method of water quality monitoring points based on the RF-C-SOM clustering algorithm, which utilizes the random forest algorithm for data dimension reduction and dataset simplification, thereby reducing the redundancy of features and significantly improving the computational efficiency and model performance of subsequent processes, as well as interpretability; meanwhile, using the clustering result of fuzzy clustering as a reference for initializing SOM weights can avoid the uncertainty of randomly selecting sample initial weight values in traditional SOM algorithms and can accelerate the optimization algorithm progress to reach a convergence state more quickly, making the clustering result more accurate and reliable.

BRIEF DESCRIPTION OF DRAWINGS

The accompanying drawings that form part of the disclosure are used to provide a further understanding of the disclosure, and the illustrative embodiments and their descriptions are used to explain the disclosure, without unduly limiting the scope of the disclosure.

DETAILED DESCRIPTION OF EMBODIMENTS

It should be noted that, the embodiments and features in the embodiments of the disclosure can be combined with each other without conflict. The following will detail the disclosure with reference to the accompanying drawings and in conjunction with the embodiment.

It should be noted that the steps illustrated in the flowchart of the accompanying drawings can be executed in a computer system, such as a set of computer-executable instructions. Moreover, although the logical sequence is shown in the flowchart, in some cases, the steps shown or described can be executed in a different order than that presented here.

Figure 1:
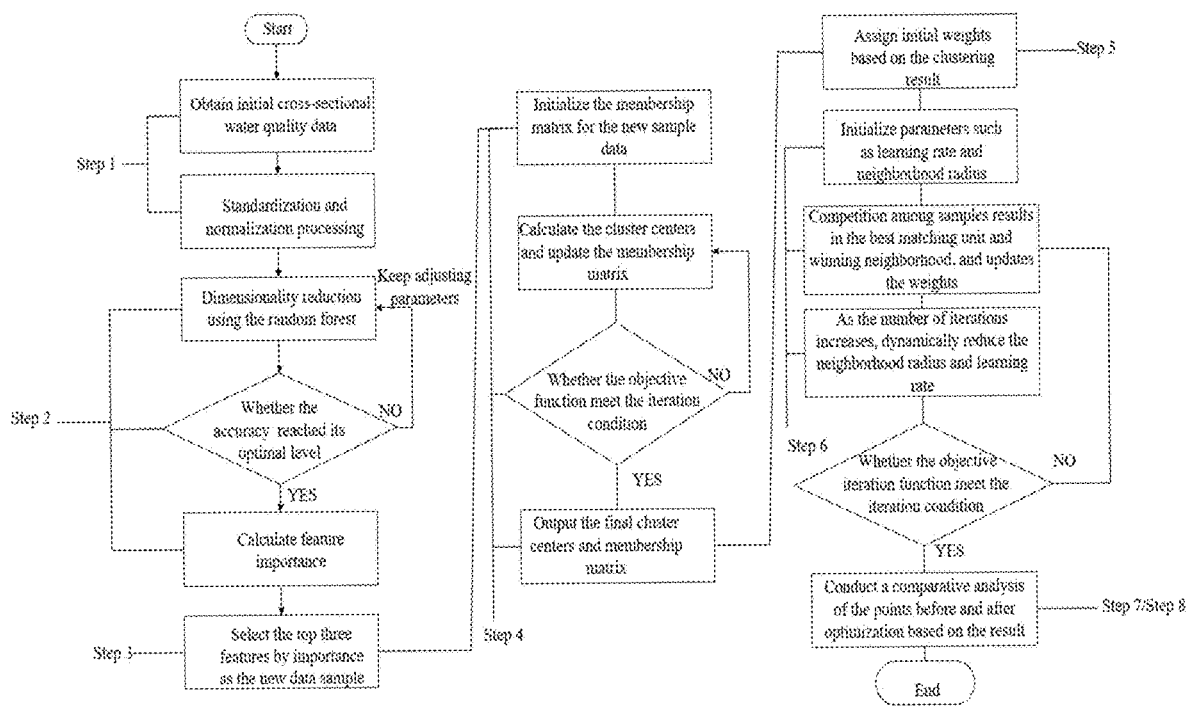
FIG. 1 illustrates a flowchart of a layout optimization method of water quality monitoring points based on a RF-C-SOM clustering algorithm according to an embodiment of the disclosure.

As shown in FIG. 1, a layout optimization method of water quality monitoring points based on a RF-C-SOM clustering algorithm is provided in an embodiment. The layout optimization method of water quality monitoring points based on the RF-C-SOM clustering algorithm includes the following step 1 to step 8.

Step 1, collected initial water quality data is preprocessed to obtain processed water quality data.

Preprocessing includes a processing of missing values and abnormal values of original data (i.e., the collected initial water quality data), as well as normalization and standardization to eliminate an impact of different data dimensions and orders of magnitude.

The initial water quality data includes potential of hydrogen (PH), dissolved oxygen, conductivity, turbidity, a permanganate index, ammonia nitrogen, total phosphorus and total nitrogen.

Step 2, the processed water quality data are used as data, and water quality categories are used as labels to train a random forest model.

Step 3, based on feature importance and an accuracy of the model (i.e., the random forest model) training, a selection of important features is conducted, and dimensionality reduction is performed.

Step 4, a fuzzy clustering is performed by using the selected features as new variables.

Step 5, based on a classification result of a water quality cross-section obtained in the step 4, initial weight values of a SOM algorithm are determined, and initial weight values of points are the same in a same category.

Step 6, neurons are initialized and a SOM model is trained based on the initial weight values.

Step 7, a point clustering result is obtained through the SOM model.

Step 8, a water quality index is evaluated by combining the initial water quality data with the point clustering result.

Preferably, in the above layout optimization method of water quality monitoring points based on the RF-C-SOM clustering algorithm, for continuous missing values of each indicator of the original data, directly deleting the continuous missing values, and for an individual missing value of each indicator of the original data, adopting an attribution method and using an average of the indicator to fill in the individual missing value of the indicator to repair the individual missing value of the indicator.

Preferably, in the above layout optimization method of water quality monitoring points based on the RF-C-SOM clustering algorithm, a single section is used as an example, the collected water quality data is organized into an original data matrix $A(a_{ij})$ with dates as rows and indicators as columns, as follows:

$$A = \begin{pmatrix} a_{11} & \cdots & a_{1j} \\ \vdots & \ddots & \vdots \\ a_{i1} & \cdots & a_{ij} \end{pmatrix} = (a_1, a_2, a_3, \ldots, a_j)(i=1,2,\ldots,n; j=1,2,\ldots,m)$$

Preferably, in the above layout optimization method of water quality monitoring points based on the RF-C-SOM clustering algorithm, in the step 1, in order to eliminate the impact of different data dimensions and orders of magnitude, data are standardized by using a Z-score method to form a standardized matrix $B(b_{ij})$ according to the formula as follows:

$$b_{ij} = \frac{a_{ij} - \overline{a_j}}{\delta_j} \quad (1)$$

(i=1, 2, . . . , n; j=1, 2, . . . , m)

In the formula (1), $a_{ij}$ represents a value of a $j^{th}$ indicator on an $i^{th}$ day, $\overline{a}_j$ represents a sample mean of the $j^{th}$ indicator, and $\delta_j$ represents a standard deviation of the $j^{th}$ indicator, also known as an unbiased estimate. At this point, in the standardized matrix B, the mean of each column of data is 0, and the variance of each column of data is 1. A processed dataset (i.e., the process data) is set as D, and a sample size of the processed dataset is set as K.

$$\overline{a_J} = \frac{1}{n}\sum_{i=1}^{n} a_{ij}$$

$$\delta_j = \sqrt{\frac{1}{n-1}\sum_{i=1}^{n}(a_{ij} - \overline{a_J})^2} \quad (j = 1, 2, \ldots, m)$$

The data of different magnitudes are transformed to a same scale to achieve standardization, and to ensure comparability of the data for a subsequent training of the random forest model.

Preferably, in the above layout optimization method of water quality monitoring points based on the RF-C-SOM clustering algorithm, the water quality data of a single section from 2021 to 2022 years are used as an example, the processed dataset D is divided into a training set T and a testing set S.

The random forest model is trained and learned by using the training set T, and a training sample set is selected from the training set T by sampling with replacement (bootstrap) method to include n samples, which is used to generate a decision tree.

When a sample size K in an original dataset (i.e., the processed dataset) is sufficiently large, the bootstrap method is used to draw samples, and approximately ⅓ of the processed data is not utilized, which is referred to as out-of-bag (oob) data. An oob data error is calculated based on the oob data, set as erroob1. Randomly, noise interference is added to a certain feature of all oob samples, and an oob data error is recalculated, set as erroob2.

A method of calculating the importance of feature variables by using an oob error (i.e., the oob data error) is:

$$\text{importance} = \sum_{i=1}^{N} \frac{(erroob2 - erroob1)}{N}$$

where N represents a number of the decision tree in a random forest.

The larger an importance value of a single feature, the greater an impact of adding noise to the feature on a sample prediction result, and the higher a level of importance.

Based on a Gini coefficient, impurities are calculated by the random forest model, and an optimal node and an optimal branching method of the decision tree are determined by selecting an optimal feature of an impurity indicator. The formula for the Gini coefficient is as follows:

$$Gini(t) = 1 - \sum_{i=0}^{c-1} p(i|t)^2$$

where c represents a number of the water quality categories, t represents a given feature node, and p(i|t) represents a proportion of a label category i at the feature node t.

The lower an impurity, the higher a degree of fitting of the decision tree to the training set.

Preferably, an accuracy of the random forest model on the training set S is calculated, and the formula is as follows:

$$\text{Accuracy} = \frac{TP + TN}{TP + TN + FP + FN}$$

where TP represents a number of positive samples that are predicted as positive, TN represents a number of negative samples that are predicted as negative, FP represents a number of negative samples that are predicted as positive, and FN represents a number of positive samples that are predicted as negative.

After optimizing parameters to improve the accuracy of the random forest model, a selection of features is conducted based on feature importance to achieve a purpose of dimensionality reduction. New variables obtained after dimensionality reduction are served as new variables for subsequent clustering.

In the step 4, the following process is undertaken for the fuzzy clustering of the new water quality data samples after dimensionality reduction.

Preferably, the new water quality data after dimensionality reduction is subjected to data standardization by using the formula (1). This step eliminates the impact of different data dimensions and ensures the effect of the clustering process.

S1, a clustering algorithm is initialized, and initial parameters and variables are determined.

The initial parameters and variables include: a cluster number C, a fuzzy weighting index m, and a maximum iteration error ε. Generally, the fuzzy weighting index m is set as 2, and the maximum iteration error ε is set as 0.001.

S2, a membership degree matrix U is initialized by using a random number between [0,1], and the membership degree matrix U must satisfy a constraint condition $\Sigma_{i=1}^{C} U_{ij} = 1$; where $U_{ij}$ represents a membership degree of a water quality sample point $x_i$ and a cluster center $C_j$.

S3, a fuzzy classification of a water quality dataset is obtained through an iterative optimization of an objective function, that is, a minimum value of the objective function under the constraint condition is obtained by using a method of Lagrange multipliers. An updated membership degree matrix U and an updated cluster center $C_j$ are calculated according to the following formulas:

$$j(U,V) = \Sigma_{i=1}^{n} \Sigma_{j=1}^{c} u_{ij}^{m} d(x_i, c_j)^2 \tag{2}$$

$$u_{ij} = \frac{1}{\sum_{k=1}^{c} \left(\frac{d(x_i, c_j)}{d(x_i, c_k)}\right)^{\frac{2}{m-1}}} \tag{3}$$

$$C_j = \frac{\sum_{i=1}^{n} u_{ij}^m x_i}{\sum_{i=1}^{n} u_{ij}^m} \tag{4}$$

where the formula (2) represents the objective function J of a Fuzzy C-Means (FCM) algorithm, and $d(x_i, c_j)$ represents an Euclidean distance between the water quality sample point $x_i$ and the cluster center $C_j$; the formula (3) represents the updated membership degree matrix U; and the formula (4) represents the updated cluster center $C_j$.

The Euclidean distance formula is:

$$d(X, C) = \sqrt{\sum_{i=1}^{n}(x_i - y_i)^2}$$

S4, S3 is repeated until the objective function J meets an iteration termination condition $\|J^l - J^{l-1}\| \leq \varepsilon$, at this point, an iterative center of the data no longer change significantly, and results of the cluster center and the data membership degree matrix are output.

Preferably, after the fuzzy clustering, the point clustering result is obtained, and the original cross-section is divided into several categories. Cross-sections that belong to a same category are all assigned a same weight value, which is used as initial values of self-organizing mapping (SOM) neurons.

Preferably, the processed water quality data and their initial weights are input into the SOM network.

A principle of a SOM algorithm is as follows.

The SOM algorithm is an unsupervised learning neural network commonly used for clustering, dimensionality reduction, and feature extraction. Its structure is simple, including an input layer (with n neurons) and a competitive layer (with x*y neurons), typically arranged as a two-dimensional grid. During a competition phase, a similarity between the input data and the weights of the neurons in a mapping layer is calculated, and a most similar neuron is selected as a best matching unit. Subsequently, weights of the best matching unit and its neighboring nodes are adjusted to make the most similar neuron be more similar to an input data. In a cooperation phase, the weights are further adjusted to form a topological structure of the entire mapping layer. The clustering effect of input data is achieved by SOM through a self-organizing mapping, which can preserve topological structure characteristics of the input data and map similar data to adjacent areas, making it widely used in clustering problems. Overall, SOM is a powerful unsupervised learning tool capable of effectively handling complex high-dimensional data.

Figure 2:
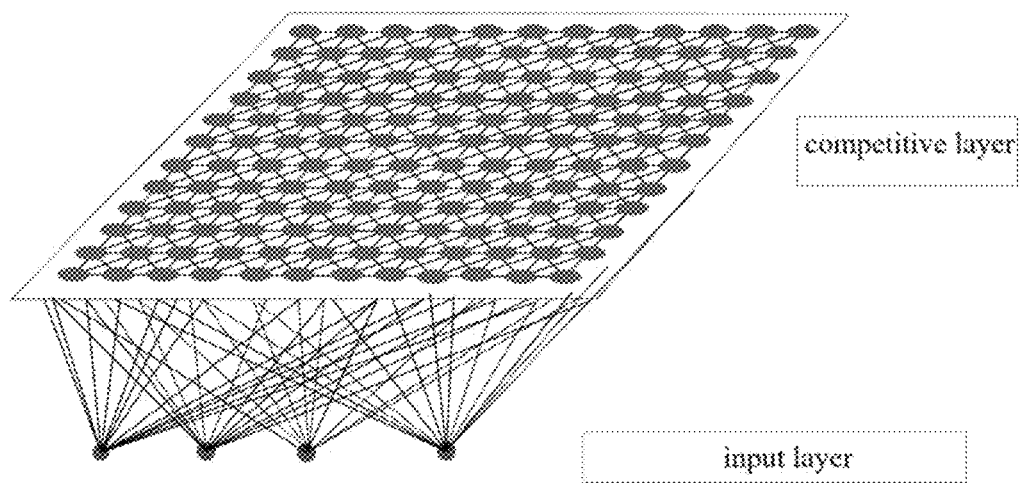
FIG. 2 illustrates a structural diagram of a self-organizing mapping network according to the embodiment of the disclosure.

The network structure diagram of the SOM algorithm is shown in FIG. 2.

The data of the input layer nodes in the algorithm is in a form of vectors:

$$M=\{(x_1),(x_2),(x_3),...,(x_n)\}$$

where $x_i=(x_{i1}, x_{i2}, x_{i3},..., x_{im})$, n represents a total number of samples, and m represents a number of feature dimensions of the samples.

A scale of the SOM is determined by a number of nodes in the competitive layer, and a two-dimensional structure is commonly used. A minimum number of nodes required for a two-dimensional competitive layer can be derived from the empirical formula, which is as follows:

$$x=y=\sqrt{5\sqrt{n}}$$

The neuron weights in the SOM competitive layer are initialized based on the clustering result of the fuzzy clustering, and samples within a same category are assigned as a same initial weight value, set as:

$$W \in R^{x*y*n}$$

Preferably, a neighborhood radius and a learning rate are initialized.

Preferably, based on the Euclidean distance formula, the distance between a random sample X and each node sample in the competitive layer is calculated. A competitive learning strategy is adopted, and the network is gradually optimized through a mutual competition among neurons.

Preferably, in the competition process, a node closest to the random sample X is recorded as the best matching unit $(c_x, c_y)$.

The weights W of all nodes within a winning neighborhood of the best matching unit must be updated. The winning neighborhood is determined by the neighborhood radius σ, with the formula as follows:

$$W_j^{k+1}=W_j^k+\eta^k g_{ij}*(x_i-W_j^k)$$

where $W_j^k$ represents a weight of a $j^{th}$ neuron node at a $k^{th}$ iteration, $\eta^k$ represents a learning rate at the $k^{th}$ iteration, and $g_{ij}$ represents an update magnitude of the $j^{th}$ neural node of a winning neighborhood corresponding to an $i^{th}$ sample. The update magnitudes can be calculated according to a neighborhood function is:

$$g(i, j) = e^{-\frac{(c_x-i)^2}{2\sigma_{(k)}^2}} e^{-\frac{(c_y-j)^2}{2\sigma_{(k)}^2}}$$

Preferably, the clustering effect is constantly influenced by the neighborhood radius σ. Similarly, a convergence speed is influenced by the learning rate η. In order to achieve a best possible effect, a dynamic shrinkage function that continuously changes values of the neighborhood radius and the learning rate is set as the number of the iterations is increased, and specific formulas are as follows:

$$\sigma_k = \frac{\sigma}{1+k/T}$$

$$\eta_k = \frac{\eta}{1+k/T}$$

where k represents a current number of the iterations, and T represents a half of a total number of the iterations.

Preferably, when the number of the iterations reaches a maximum number of the iterations, the algorithm is ended.

The disclosure provides the layout optimization method of water quality monitoring points based on the RF-C-SOM clustering algorithm, which utilizes the random forest algorithm for data dimension reduction and dataset simplification, reducing the redundancy of features and significantly improving the computational efficiency, model performance, and interpretability of subsequent processes. At the same time, the clustering result of fuzzy clustering is used as a reference for initializing the SOM weights, which not only avoids the uncertainty of randomly selecting sample initial weight values in traditional SOM algorithms but also accelerates the optimization algorithm progress to reach a convergence state more quickly, making the clustering result more accurate and reliable.

The above is merely the preferred embodiment of the disclosure, but the scope of protection of the disclosure is not limited thereto. Those skilled in the art, within the technical scope disclosed by the disclosure, can easily think of variations or substitutions, which should all be covered within the scope of protection of the disclosure. Therefore, the scope of protection of the disclosure should be determined by the scope of the claims.

What is claimed is:

1. A layout optimization method of water quality monitoring points based on a random forest—clustering—self-organizing mapping (RF-C-SOM) clustering algorithm, comprising:

step 1, preprocessing collected initial water quality data to obtain preprocessed water quality data, wherein the preprocessing collected initial water quality data to obtain preprocessed water quality data comprises:

for continuous missing values of each indicator of the collected initial water quality data, directly deleting the continuous missing values, and for an individual missing value of each indicator of the collected initial water quality data, adopting an attribution method and using an average of the indicator to fill in the individual missing value of the indicator to repair the individual missing value of the indicator, thereby obtaining processed initial water quality data; and in order to eliminate an impact of different data dimensions and orders of magnitude, performing a Z-score standardization on the processed initial water quality data to obtain the preprocessed water quality data according to a formula as follows:

$$b_{ij} = \frac{a_{ij} - \overline{a_j}}{\delta_j}$$

where $a_{ij}$ represents a value of a $j^{th}$ indicator on an $i^{th}$ day, $\overline{a}_j$ represents a sample mean of the $j^{th}$ indicator, and $\delta_j$ represents a standard deviation of the $j^{th}$ indicator;

step 2, training a random forest model by taking the preprocessed water quality data as data and water quality categories as labels to determine feature importance of water quality indicators;

step 3, based on the feature importance and an accuracy of the random forest model training, selecting important features and performing dimensionality reduction on the preprocessed water quality data to obtain dimension-reduced data; wherein the selecting important features and performing dimensionality reduction on the preprocessed water quality data to obtain dimension-reduced data comprises:

dividing the preprocessed water quality data into a training set and a test set in a ratio of 7:3, and using the water quality categories as the labels to train the random forest model;

sampling from all training samples to obtain a sample set by using a bootstrap sampling method with replacement, and using the sample set to generate a decision tree; calculating impurities based on a Gini coefficient, determining an optimal node and an optimal branching method of the decision tree by selecting an optimal feature of an impurity indicator, and calculating accuracy of the random forest model; and calculating importance of feature variables by utilizing an out-of-bag (oob) data error generated by oob data to obtain top-ranked feature variables in terms of the importance;

wherein calculating the impurities based on the Gini coefficient comprises:

$$Gini(t) = 1 - \sum_{i=0}^{c-1} p(i|t)^2$$

where c represents a number of the water quality categories, t represents a given feature node, and p(i|t) represents a proportion of a label category i at the feature node t;

wherein calculating the importance of feature variables by utilizing the oob data error generated by the oob data comprises:

$$importance = \sum_{i=1}^{N} \frac{(erroob2 - erroob1)}{N}$$

where N represents a number of the decision tree in a random forest, erroob1 represents the oob data error calculated based on the oob data, and erroob2 represents oob data error recalculated after randomly introducing noise disturbance to a certain feature of all oob samples;

step 4, performing a fuzzy clustering on the dimension-reduced data to obtain a classification result of a water quality cross-section, wherein the performing a fuzzy clustering on the dimension-reduced data to obtain a classification result of a water quality cross-section comprises:

S1, initializing a clustering algorithm, and determining initial parameters and variables;

S2, initializing a membership degree matrix U by using a random number between [0,1], and making the membership degree matrix U satisfy a constraint condition $\Sigma_{i=1}^{C} U_{ij} = 1$, where $U_{ij}$ represents a membership degree of a water quality sample point $x_i$ and a cluster center $C_j$;

S3, obtaining a fuzzy classification of the dimension-reduced data through an iterative optimization of an objective function, using a method of Lagrange multipliers to obtain a minimum value of the objective function under the constraint condition, and calculating an updated membership degree matrix U and an updated cluster center $C_j$ according to formulas as follows:

$$j(U,V) = \Sigma_{i=1}^{n} \Sigma_{j=1}^{c} u_{ij}^{m} d(x_i, c_j)^2 \quad (1)$$

$$u_{ij} = \frac{1}{\sum_{k=1}^{c} \left(\frac{d(x_i, c_j)}{d(x_i, c_k)}\right)^{\frac{2}{m-1}}} \quad (2)$$

$$C_j = \frac{\sum_{i=1}^{n} u_{ij}^{m} x_i}{\sum_{i=1}^{n} u_{ij}^{m}} \quad (3)$$

where the formula (1) represents the objective function J of a Fuzzy C-Means (FCM) algorithm, V represents a cluster center set, m represents a fuzzy weighting index, and $d(x_i, c_j)$ represents an Euclidean distance between the water quality sample point $x_i$ and the cluster center $C_j$; the formula (2) represents the updated membership degree matrix U; and the formula (3) represents the updated cluster center $C_j$;

wherein a formula of the Euclidean distance is:

$$d(X, C) = \sqrt{\sum_{i=1}^{n} (x_i - y_i)^2}$$

where d(X,C) represents the Euclidean distance between a water quality sample point X and a cluster center C, $x_i$ (i=1, 2, ..., n) is a $i^{th}$ coordinate of the water quality sample point X, and $y_i$ (i=1, 2, ..., n) is a $i^{th}$ coordinate of the cluster center C; and S4, repeating S3 until the objective function J meets an iteration termination condition $\|J^l - J^{l-1}\| \le \varepsilon$, such that at this time, an iterative center of data is no longer changing significantly, and outputting results of the cluster center and the data membership degree matrix;

step 5, based on the classification result of the water quality cross-section, determining initial weight values of a self-organizing mapping algorithm;

step 6, based on the initial weight values, initializing neurons and training a self-organizing mapping network model;

step 7, obtaining a point clustering result through the self-organizing mapping network model; and step 8, evaluating a water quality index by combining the initial water quality data with the point clustering result.

2. The layout optimization method of water quality monitoring points as claimed in claim 1, wherein the initial water quality data comprise potential of hydrogen (PH), dissolved oxygen, conductivity, turbidity, a permanganate index, ammonia nitrogen, total phosphorus and total nitrogen.

3. The layout optimization method of water quality monitoring points as claimed in claim 1, wherein the obtaining the point clustering result through the self-organizing mapping network model comprises:

initializing a two-dimensional grid structure, wherein each node represents a cluster center;

initializing samples in a dataset based on a fuzzy clustering result, wherein samples belonging to a same category are assigned a same initial weight vector, and then updating weights through a network topology structure;

in each iteration, selecting an input sample, finding a node closest to a node corresponding to the input sample, and adjusting update magnitudes of a best matching unit and its neighboring nodes; and wherein through continuous iteration, adjacent nodes form clusters in a feature space, ultimately creating a topological mapping of the data.

4. The layout optimization method of water quality monitoring points as claimed in claim 3, wherein updating the weights comprises:

$$W_j^{k+1} = W_j^k + \eta^k g_{ij} * (x_i - W_j^k)$$

where $W_j^k$ represents a weight of a $j^{th}$ neuron node at a $k^{th}$ iteration, $\eta^k$ represents a learning rate at the $k^{th}$ iteration, and $g_{ij}$ represents an update magnitude of the $j^{th}$ neural node of a winning neighborhood corresponding to an $i^{th}$ sample.

5. The layout optimization method of water quality monitoring points as claimed in claim 4, wherein calculating the update magnitudes of nodes within a winning neighborhood according to a neighborhood function comprises:

$$g(i, j) = e^{-\frac{(c_x - i)^2}{2\sigma_{(k)}^2}} e^{-\frac{(c_y - j)^2}{2\sigma_{(k)}^2}}$$

where $(c_x, c_y)$ represents the best matching unit, and $\sigma(k)$ represents a winning radius at the $k^{th}$ iteration.

* * * * *